(12) United States Patent
Lee et al.

(10) Patent No.: US 10,420,483 B2
(45) Date of Patent: Sep. 24, 2019

(54) APPARATUS AND METHOD FOR MEASURING BIOELECTRIC IMPEDANCE USING THREE-ELECTRODE SENSOR

(71) Applicant: SAMSUNG ELECTRONICS CO., LTD., Suwon-si (KR)

(72) Inventors: Yeol Ho Lee, Anyang-si (KR); Kak Namkoong, Seoul (KR); Myoung Hoon Jung, Bucheon-si (KR); Young Jun Koh, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 291 days.

(21) Appl. No.: 15/363,293

(22) Filed: Nov. 29, 2016

(65) Prior Publication Data

US 2017/0172452 A1 Jun. 22, 2017

(30) Foreign Application Priority Data

Dec. 17, 2015 (KR) .......................... 10-2015-0181192

(51) Int. Cl.
| | |
|---|---|
| *A61B 5/053* | (2006.01) |
| *A61B 5/00* | (2006.01) |
| *A61B 5/0402* | (2006.01) |
| *A61B 5/0408* | (2006.01) |

(52) U.S. Cl.
CPC .......... *A61B 5/0537* (2013.01); *A61B 5/0022* (2013.01); *A61B 5/04028* (2013.01); *A61B 5/0533* (2013.01); *A61B 5/4869* (2013.01); *A61B 5/4872* (2013.01); *A61B 5/4875* (2013.01); *A61B 5/681* (2013.01); *A61B 5/6824* (2013.01); *A61B 5/6898* (2013.01); *A61B 5/742* (2013.01); *A61B 5/7405* (2013.01); *A61B 5/7455* (2013.01); *A61B 5/04085* (2013.01)

(58) Field of Classification Search
CPC ............ A61B 5/681; A61B 2560/0468; A61B 5/04085; A61B 5/04325; A61B 5/053; A61B 5/0535; A61B 5/0537; A61B 5/6843; A61B 5/6824; A61B 5/4875; A61B 5/4872; A61B 5/4869; A61N 2001/083
USPC ..................................... 600/536, 547; 607/8
See application file for complete search history.

(56) References Cited

U.S. PATENT DOCUMENTS

| | | | | |
|---|---|---|---|---|
| 7,783,345 | B2* | 8/2010 | Skrabal | A61B 5/0535 600/508 |
| 7,818,058 | B2 | 10/2010 | Mentelos | |
| 8,743,079 | B2* | 6/2014 | Norieda | G06F 1/163 345/156 |
| 2010/0076331 | A1* | 3/2010 | Chan | A61B 5/681 600/522 |
| 2013/0261414 | A1 | 10/2013 | Tal et al. | |

FOREIGN PATENT DOCUMENTS

| | | |
|---|---|---|
| JP | 2001078978 A | 3/2001 |
| JP | 3396677 B2 | 4/2003 |
| JP | 4679993 B2 | 5/2011 |
| KR | 100542795 B1 | 1/2006 |

* cited by examiner

*Primary Examiner* — David J. McCrosky
(74) *Attorney, Agent, or Firm* — Sughrue Mion, PLLC

(57) ABSTRACT

An apparatus and method for measuring a bioelectric impedance is provided. The apparatus may measure the bioelectric impedance using three electrodes. The apparatus may measure the bioelectric impedance by compensating for a change of a contact impedance.

14 Claims, 7 Drawing Sheets

APPARATUS AND METHOD FOR MEASURING BIOELECTRIC IMPEDANCE USING THREE-ELECTRODE SENSOR

CROSS-REFERENCE TO RELATED APPLICATION

This application claims priority from Korean Patent Application No. 10-2015-0181192, filed on Dec. 17, 2015 in the Korean Intellectual Property Office, the disclosure of which is incorporated herein by reference in its entirety.

BACKGROUND

1. Field

Apparatuses and methods consistent with exemplary embodiments relate to bioelectric impedance measurement technology, and more particularly to measuring a bioelectric impedance using a three-electrode sensor.

2. Description of Related Art

Various medical apparatuses are being developed in order to diagnose a health condition of a patient. In the process of diagnosing the health, the importance of medical apparatuses for measuring a bioelectric signal of the patient is being highlighted due to convenience of the patient and rapidity of a health diagnosis result, etc.

Particularly, a bioelectric impedance may be used for monitoring a health or emotional condition of a body, and recently, various studies for miniaturization of an apparatus for measuring a bioelectric impedance are being progressed.

SUMMARY

One or more exemplary embodiments provide an apparatus and method for measuring a bioelectric impedance using three electrodes.

According to an aspect of an exemplary embodiment, there is provided a bioelectric impedance measurement apparatus including: a first electrode; a second electrode; a third electrode; a first voltage measurer configured to measure a first voltage between the second electrode and the third electrode generated by a current applied to an object through the first electrode and the third electrode, a short-circuit unit configured to short-circuit the first electrode to the second electrode, a second voltage measurer configured to measure a second voltage between the short-circuited first electrode and the third electrode generated by a current applied to the object through the short-circuited first electrode and the third electrode, and an impedance calculator configured to calculate a resulting impedance value of the object based on the first voltage and the second voltage.

The bioelectric impedance measurement apparatus may be implemented as a mobile device.

The bioelectric impedance measurement apparatus may be implemented as a wristwatch-type wearable device, and the first electrode and the second electrode may be disposed on a back surface of a body of the wristwatch-type wearable device.

The third electrode may be disposed on a front surface of the body of the wristwatch-type wearable device.

The third electrode may be disposed on a strap of the wristwatch-type wearable device.

The impedance calculator may calculate a first impedance based on the first voltage and the current applied to the object through the first electrode and the third electrode, calculate a second impedance based on the second voltage and the current applied to the object through the short-circuited first electrode and the third electrode, and calculate the resulting impedance value of the object based on the first impedance and the second impedance.

The impedance calculator may calculate the resulting impedance value based on a bioelectric impedance calculation equation defining a relationship of the impedance of the object, the first impedance, and the second impedance.

The bioelectric impedance calculation equation may be derived from a contact impedance generated by a contact between each electrode and the object.

The first, second and third electrodes may further be used to measure at least one of an electrocardiogram (ECG) and galvanic skin response (GSR).

The bioelectric impedance measurement apparatus may further include a power supply configured to apply a predetermined current to the object through the first electrode and the third electrode or the short-circuited first electrode and the third electrode.

According to an aspect of another exemplary embodiment, there is provided a bioelectric impedance measurement method including: applying a current to an object through a first electrode and a third electrode, measuring a first voltage between a second electrode and the third electrode, short-circuiting the first electrode to the second electrode, applying a current to the object through the short-circuit first electrode and the third electrode, measuring a second voltage between the short-circuited first electrode and the third electrode, and calculating a resulting impedance value of the object based on the first voltage and the second voltage.

The calculating the resulting impedance value of the object may include, calculating a first impedance based on the first voltage and the current applied to the object through the first electrode and the third electrode, calculating a second impedance based on the second voltage and the current applied to the object through the short-circuited first electrode and the third electrode, and calculating the resulting impedance value of the object based on the first impedance and the second impedance.

The calculating the resulting impedance value of the object may use a bioelectric impedance calculation equation defining a relationship of the resulting impedance value of the object, the first impedance, and the second impedance.

The bioelectric impedance calculation equation may be derived from a contact impedance generated by a contact between each electrode and the object.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
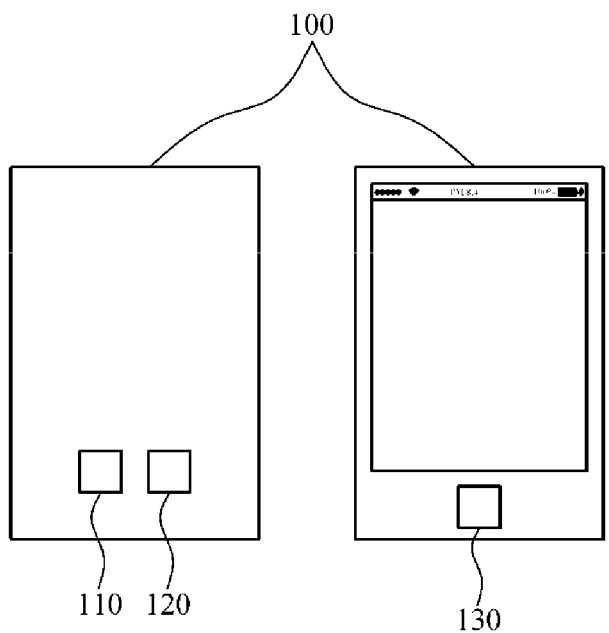
FIG. 1 is a diagram illustrating an electrode placement of a mobile device according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

Throughout the drawings and the detailed description, unless otherwise described, the same drawing reference numerals should be understood to refer to the same elements, features, and structures. The relative size and depiction of these elements may be exaggerated for clarity, illustration, and convenience.

As is traditional in the field of the inventive concept, certain elements of exemplary embodiments are described, and illustrated in the drawings, in terms of functional blocks, units and/or modules. Those skilled in the art will appreciate that these blocks, units and/or modules are physically implemented by electronic (or optical) circuits such as logic circuits, discrete components, microprocessors, hard-wired circuits, memory elements, wiring connections, and the like, which may be formed using semiconductor-based fabrication techniques or other manufacturing technologies. In the case of the blocks, units and/or modules being implemented by microprocessors or similar, they may be programmed using software (e.g., microcode) to perform various functions discussed herein and may optionally be driven by firmware and/or software. Alternatively, each block, unit and/or module may be implemented by dedicated hardware, or as a combination of dedicated hardware to perform some functions and a processor (e.g., one or more programmed microprocessors and associated circuitry) to perform other functions. Also, each block, unit and/or module of the embodiments may be physically separated into two or more interacting and discrete blocks, units and/or modules without departing from the scope of the inventive concepts. Further, the blocks, units and/or modules of the embodiments may be physically combined into more complex blocks, units and/or modules without departing from the scope of the inventive concept.

FIG. 1 is a diagram illustrating an electrode placement of a mobile device according to an exemplary embodiment.

A mobile device 100 may be a device which measures a bioelectric impedance, a bioelectric signal (for example, an electrocardiogram (ECG), galvanic skin response (GSR), etc.) in addition to the bioelectric impedance, and may include a mobile phone, a smart phone, a tablet personal computer (PC), a notebook computer, a personal digital assistant (PDA), a portable multimedia player (PMP), a navigation unit, an MP3 player, a digital camera, a wearable device, etc. However, the mobile device is not limited to the examples described above, and may include various devices.

According to an exemplary embodiment, the mobile device 100 may measure an impedance of an object using a bioelectrical impedance analysis (BIA) method of measuring an electric impedance of the object by applying a current to the object. Here, the object may mean a user or a body of the user.

The mobile device 100 may include three electrodes 110, 120, and 130.

A first electrode 110 may be a current applying electrode used for applying a current to an object, a second electrode 120 may be a voltage measuring electrode used for measuring a voltage of the object, and a third electrode 130 may be a common electrode used for applying a current to the object and also measuring the voltage of the object.

The three electrodes 110, 120, and 130 may be disposed in various forms on the mobile device 100. That is, the three electrodes 110, 120, and 130 may be disposed in various forms by considering convenience of the user, and a design, a shape and a structure of the mobile device 100.

For example, as shown in FIG. 1, the first electrode 110 and the second electrode 120 may be disposed on a back surface (or a back side, or a rear surface) of the mobile device 100, and the third electrode 130 may be disposed on a front surface of the mobile device 100. In this case, the electrodes 110, 120, and 130 may be disposed in an area excluding a portion in which an antenna of the mobile device 100 is disposed so as to prevent it from obstructing transmission and reception of a radio wave.

Further, according to an exemplary embodiment, a logo engraved in the mobile device 100 may be used as an electrode, and the electrodes may be disposed on an edge of the mobile device.

Meanwhile, the electrodes 110, 120, and 130 may be configured in various shapes. In an example of FIG. 1, the three electrodes 110, 120, and 130 are illustrated in a rectangular shape, but may have a round shape, a diamond shape, a triangular shape, etc., and each of the three electrodes may be configured to have a different shape.

Further, the electrodes 110, 120, and 130 may be disposed to easily come into contact with an object by being disposed at a position higher than a surface of the mobile device 100, and may have a pattern such as a dot pattern, a hair pattern, an engraved pattern, etc. so that the user may easily recognize the position of the electrode.

According to an exemplary embodiment, the electrodes 110, 120, and 130 may be configured in various materials. For example, the electrodes 110, 120, and 130 may be configured using metal, conductive rubber, conductive plastic, conductive fibers, conductive ceramic, etc. Further, when using a metal, the electrodes 110, 120, and 130 may be coated with titanium nitride (TiN), titanium carbon nitride (TiCN), or chromium nitride (CrN) so as to increase surface conductivity and scratch resistance of the electrode surface.

Meanwhile, the three electrodes 110, 120, and 130 of the mobile device 100 may be used for measuring a bioelectric impedance and also a bioelectric signal (for example, the ECG, the GSR, etc.) in addition to the bioelectric impedance.

Figure 2:
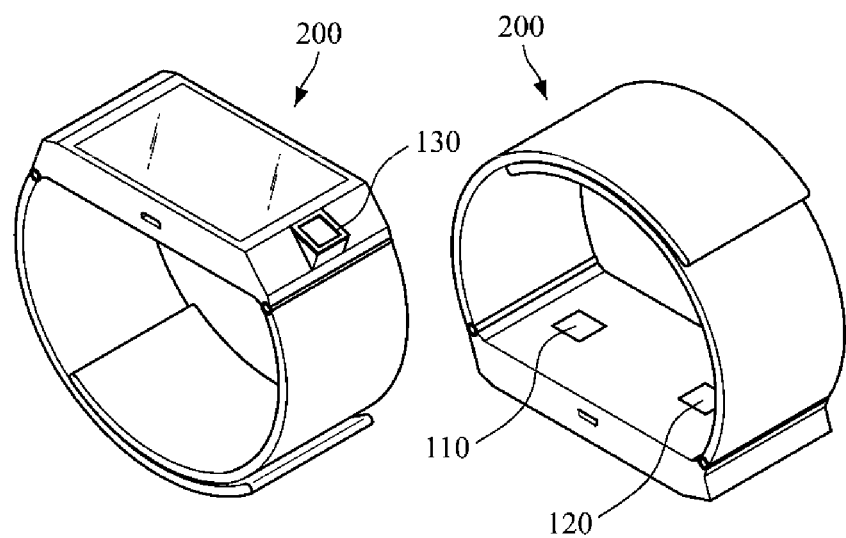
FIG. 2 is a diagram illustrating an electrode placement of a wristwatch-type wearable device according to an exemplary embodiment.

FIG. 2 is a diagram illustrating an electrode placement of a wristwatch-type wearable device according to an exemplary embodiment. FIG. 2 illustrates an example in which the mobile device 100 shown in FIG. 1 is implemented as the wristwatch-type wearable device.

Referring to FIG. 2, the first electrode 110 and the second electrode 120 may be disposed on a back surface (or a back side or a rear surface) of a body of the device which is in contact with skin of a user so as to naturally come into contact with the skin of the user when wearing a device 200. Further, as shown in FIG. 2, the first electrode 110 and the second electrode 120 may be disposed to be spaced apart from each other by a predetermined interval in the same direction as a length of a strap. In other words, the first electrode 110 and the second electrode 120 may be disposed to be spaced apart from each other by the predetermined interval in the longitudinal direction of the strap and also in the longitudinal direction of the body of the wearable device. However, the placement of the first and second electrodes 110 and 120 is not limited thereto. For example, the first and second electrodes 110 and 120 may be disposed to be spaced apart from each other by the predetermined interval in a direction vertical to a length direction of the strap, etc., and may be disposed in various ways.

The third electrode 130 may be disposed on a front surface of the body of the device. The third electrode 130, as shown in FIG. 2, may be disposed at a lower portion of the surface so as to prevent the third electrode from obstructing a display. However, the placement of the third electrode 130 is not limited thereto, and the third electrode 130 may be disposed in an upper front portion, a left front portion, or a right front portion of the body of the device, and may be disposed in a right side or a left side of the body of the device. Further, the third electrode 130 may be disposed on the strap.

Figure 3:
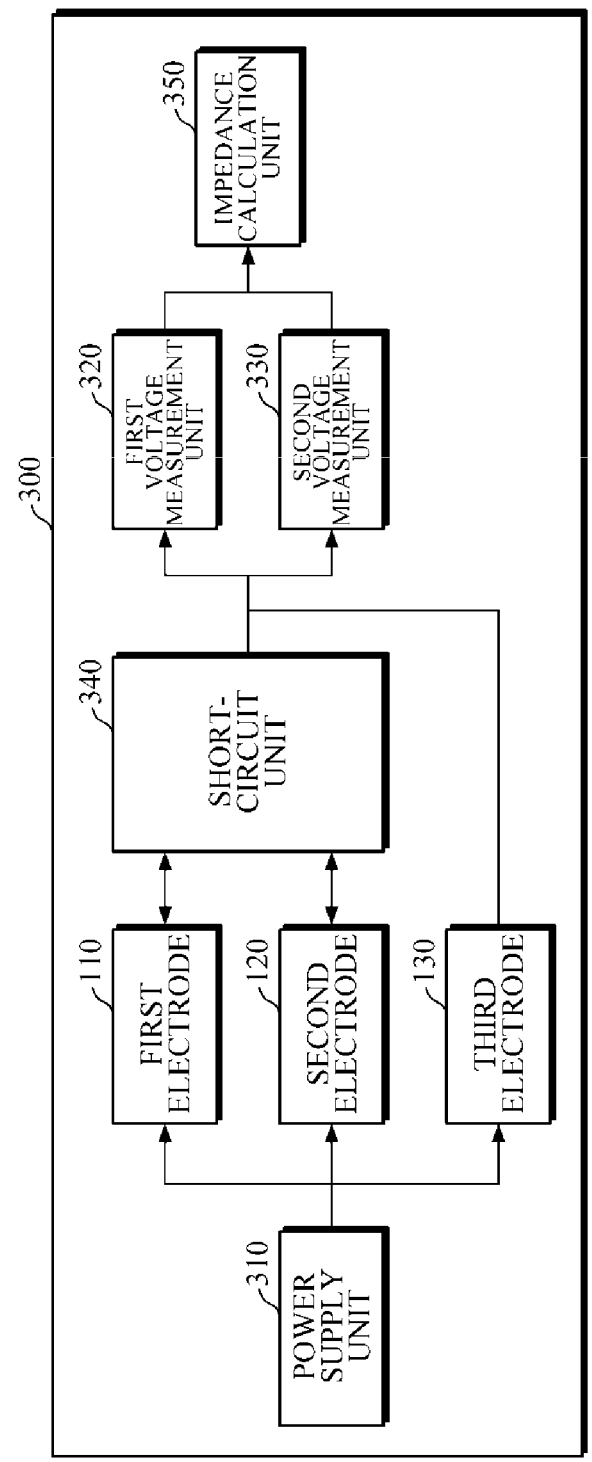
FIG. 3 is a diagram illustrating a bioelectric impedance measurement apparatus according to an exemplary embodiment.

FIG. 3 is a diagram illustrating a bioelectric impedance measurement apparatus according to an exemplary embodiment. According to an exemplary embodiment, a bioelectric impedance measurement apparatus 300 may be implemented as the mobile device 100 shown in FIG. 1, or the wristwatch-type wearable device 200 shown in FIG. 2.

When the bioelectric impedance measurement apparatus 300 is implemented as a small device such as the mobile device, since a dimension of the electrode is decreased, a dimension in which skin of the object is in contact with the electrode may be decreased, and thus a contact impedance generated according to the contact of the electrode and the object may be increased. The increase of the contact impedance may obstruct the impedance measurement of the object, and thus accuracy of the impedance measurement may be decreased.

Further, since a four-electrode method using two current applying electrodes and two voltage measuring electrodes needs at least four electrodes, the method has a limitation when applied to a small device which has insufficient space for the placement of the electrodes.

According to an exemplary embodiment, the bioelectric impedance measurement apparatus 300 may measure an impedance of an object by compensating for a change of a contact impedance generated due to the dimensional decrease of the electrode using the three electrodes.

Referring to FIG. 3, the bioelectric impedance measurement apparatus 300 may include the three electrodes 110, 120, and 130, a power supply unit (e.g., power supply) 310, a first voltage measurement unit 320, a second voltage measurement unit 330, a short-circuit unit 340, and an impedance calculation unit 350. The impedance calculation unit 350 may be implemented by a processor.

The first electrode 110 may be a current applying electrode used for applying a current to an object, a second electrode 120 may be a voltage measuring electrode used for measuring a voltage of the object, and a third electrode 130 may be a common electrode used for applying a current to the object and also measuring the voltage of the object. Since the placement of the three electrodes 110, 120, and 130 was described in detail with reference to FIGS. 1 and 2, a detailed description thereof will be omitted.

The power supply unit 310 may apply a predetermined current to the object through the three electrodes 110, 120, and 130. For example, the power supply unit 310 may apply the predetermined current to the object through the third electrode 130. Further, after the first electrode 110 and the second electrode 120 are short-circuited, the power supply unit 310 may apply the predetermined current to the object through the short-circuited first electrode (or the short-circuited second electrode) and the third electrode 130. In this case, the predetermined current may be an alternating current (AC) having a frequency of 1 Hz to 1 GHz.

The first voltage measurement unit 320 may measure a voltage (hereinafter, it may be referred to as a first voltage) of both ends of the second and third electrodes 120 and 130 generated by the current applied to the object through the first electrode 110 and the third electrode 130.

The short-circuit unit 340 may allow the first and second electrodes 110 and 120 to be short-circuited. The short-circuit unit 340 may operate the three electrodes 110, 120, and 130 as if they were two electrodes by allowing the first and second electrodes 110 and 120 to be short-circuited.

The second voltage measurement unit 330 may measure a voltage (hereinafter, it may be referred to as a second voltage) of both ends of the short-circuited first electrode (or the short-circuited second electrode) and the third electrode 130 generated by the current applied to the object through the short-circuited first electrode (or the short-circuited second electrode) and the third electrode 130.

Meanwhile, the first voltage measurement unit 320 and the second voltage measurement unit 330 may include a digital multi-meter for measuring the voltage of both ends of the electrodes.

The impedance calculation unit 350 may calculate the impedance of the object based on the first voltage and the second voltage. For example, the impedance calculation unit 350 may calculate a first impedance using the current applied to the object through the first electrode 110 and the third electrode 130 and the first voltage, and calculate a second impedance using the current applied to the object through the short-circuited first electrode (or the short-circuited second electrode) and the third electrode 130 and the second voltage. Further, the impedance calculation unit 350 may calculate the impedance of the object based on the first impedance, the second impedance, and a bioelectric impedance calculation equation.

The bioelectric impedance calculation equation may define a relationship of the first impedance, the second impedance, and a bioelectric impedance, and be derived by considering the contact impedance generated by the contact of each electrode and the object. For example, the bioelectric impedance calculation equation may be expressed by Equation 1.

$$Z_m = \frac{Z_1 Z_i^2 + Z_2 Z_1 Z_i - 2bZ_2 Z_i^2 + 2bZ_1 Z_i^2}{Z_1 Z_i + Z_i^2 - Z_2 Z_1 - Z_2 Z_i} \quad \text{[Equation 1]}$$

Here, $Z_m$ represents the impedance of the object, $Z_1$ represents the first impedance, $Z_2$ represents the second impedance, $Z_i$ represents an internal resistance of the voltage measurement unit, b represents a weight of the contact impedance of the third electrode which is commonly used for applying the current and measuring the voltage. In this case, b may be experimentally determined.

Figure 4A:
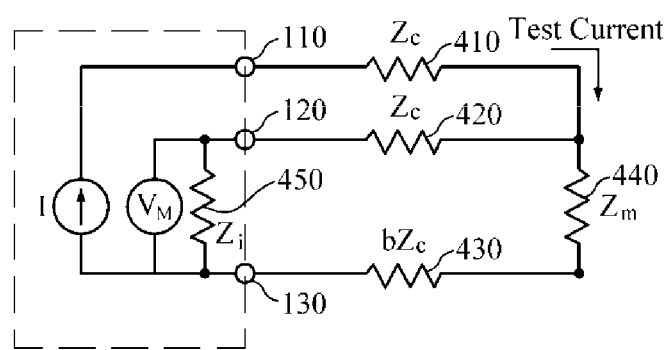
FIGS. 4A and 4B are diagrams for describing a process of deriving a bioelectric impedance calculation equation.
Figure 4B:
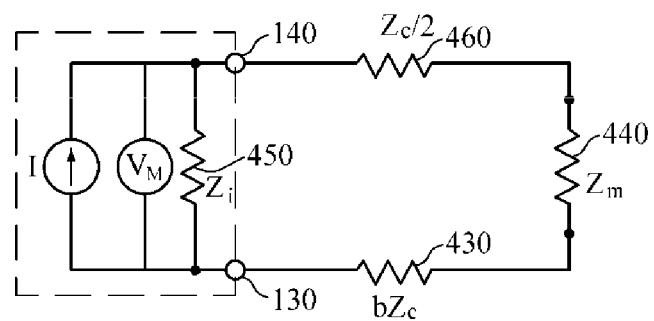

FIGS. 4A and 4B are diagrams for describing a process of deriving a bioelectric impedance calculation equation. In detail, FIG. 4A is a diagram illustrating an equivalent circuit when measuring a first voltage, and FIG. 4B is a diagram illustrating an equivalent circuit when measuring a second voltage.

Referring to FIG. 4A, the equivalent circuit when measuring the first voltage may be illustrated by a contact impedance $Z_c$ 410 generated by the contact between the first electrode 110 and an object, a contact impedance $Z_c$ 420 generated by the contact between the second electrode 120 and the object, a contact impedance $bZ_c$ 430 generated by the contact between the third electrode 130 and the object, an impedance $Z_m$ 440 of the object, and an internal impedance $Z_i$ 450 of the voltage measurement unit.

When the power supply unit 310 applies an output current I to the object through the first electrode 110 and the third electrode 130, a first voltage $V_1$ measured between the second electrode 120 and the third electrode 130 may be expressed by Equation 2, and a first impedance $Z_1$ calculated in Equation 2 may be expressed by Equation 3.

$$V_1 = I \frac{Z_i}{1 + \frac{Z_c + Z_i}{bZ_c + Z_m}} \quad \text{[Equation 2]}$$

$$Z_1 = \frac{V_1}{I} = \frac{Z_i}{1 + \frac{Z_c + Z_i}{bZ_c + Z_m}} \quad \text{[Equation 3]}$$

Here, b may be the weight of the contact impedance of the third electrode which is commonly used for applying the current and measuring the voltage, and it may be experimentally determined.

Referring to FIG. 4B, when measuring the second voltage, the contact impedance $Z_c$ 410 and the contact impedance $Z_c$ 420 which are connected in parallel may be added to the equivalent circuit when measuring the first voltage since the first electrode 110 and the second electrode 120 are short-circuited. That is, the equivalent circuit when measuring the second voltage may be illustrated by a contact impedance $$\frac{Z_c}{2}$$

460 generated by the contact of a short-circuited first electrode (or a short-circuited second electrode) 140 and the object, a contact impedance $bZ_c$ 430 generated by the contact of the third electrode 130 and the object, an impedance $Z_m$ 440 of the object, and an internal impedance $Z_i$ 450 of the voltage measurement unit.

When the power supply unit 310 applies the output current I to the object through the short-circuited first electrode (or the shorted-circuited second electrode) 140 and the third electrode 130, a second voltage $V_2$ measured between the short-circuited first electrode (or the shorted-circuited second electrode) 140 and the third electrode 130 may be expressed by Equation 4, and a second impedance $Z_2$ calculated in Equation 4 may be expressed by Equation 5.

$$V_2 = I \frac{1}{\frac{1}{Z_m + (b + \frac{1}{2})Z_c} + \frac{1}{Z_i}} \quad \text{[Equation 4]}$$

$$Z_2 = \frac{V_2}{I} = \frac{1}{\frac{1}{Z_m + (b + \frac{1}{2})Z_c} + \frac{1}{Z_i}} \quad \text{[Equation 5]}$$

The bioelectric impedance calculation equation of Equation 1 may be derived from Equations 3 and 5.

Figure 5:
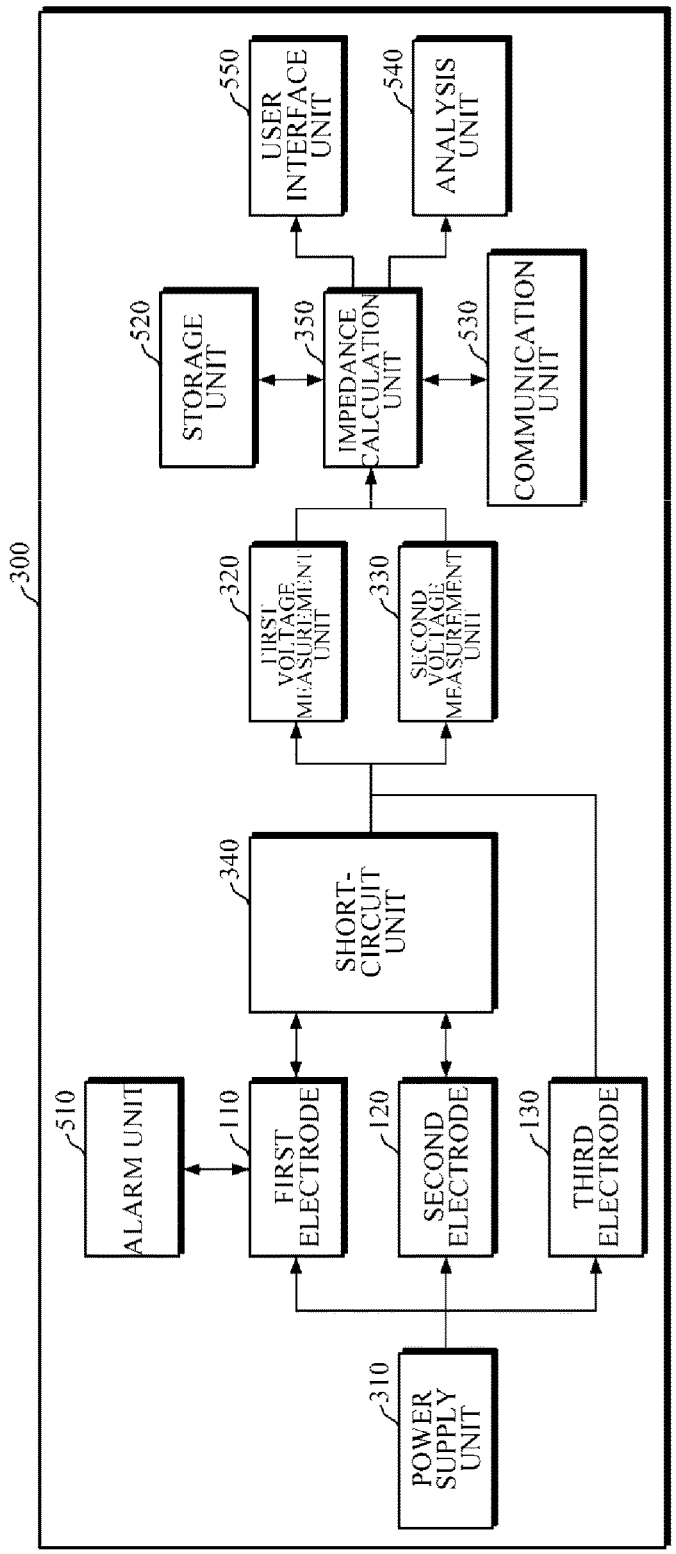
FIG. 5 is a block diagram illustrating a bioelectric impedance measurement apparatus according to another exemplary embodiment.

FIG. 5 is a block diagram illustrating a bioelectric impedance measurement apparatus according to another exemplary embodiment.

Referring to FIG. 5, a bioelectric impedance measurement apparatus 500 may further include an alarm unit 510, a storage unit (e.g., storage or memory) 520, a communication unit 530, an analysis unit 540, and a user interface unit 550 when compared with the bioelectric impedance measurement apparatus 300. The alarm unit 510, the communication unit 530, the analysis unit 540, and the user interface unit 500 may be implemented by one or more processors.

The alarm unit 510 may determine a contact condition between each of the electrodes 110, 120, and 130 of the bioelectric impedance measurement apparatus 500 and an object, and output an alarm message when the contact condition is not good. According to another exemplary embodiment, the contact condition between each of the electrodes 110, 120, and 130 and the object may be determined based on an electrical resistance between the electrodes 110, 120, and 130 or a pressure applied to each of the electrodes 110, 120, or 130. For this, the alarm unit 510 may include a pressure sensor.

The alarm unit 510 may output the alarm message in various ways. For example, the alarm unit 510 may output the alarm message using a tactile method such as vibration, etc., an auditory method such as a sound, etc. and a visual method, etc. through the user interface unit 550.

The storage unit 520 may store a program for operating and controlling the bioelectric impedance measurement apparatus 500, and store input and output data. For example, the storage unit 520 may store a program for an impedance estimation performed in the impedance calculation unit 350 and/or information related to a bioelectric impedance estimation equation. Further, the storage unit 520 may store voltage measurement results of the first voltage measurement unit 320 and the second voltage measurement unit 330 needed for the operation of the impedance calculation unit 350.

The storage unit 520 may include a storage medium of at least one-type among a flash memory type, a hard disk type, a multimedia card micro type, a card type memory (for example, secure digital (SD) or extreme digital (XD) memory, etc.), a random access memory (RAM), a static RAM (SRAM), a read-only memory (ROM), an electrically erasable and programmable ROM (EEPROM), a programmable ROM (PROM), a magnetic memory, a magnetic disk, and an optical disk.

The communication unit 530 may perform communication with an external device. The communication unit 530 may transmit a bioelectric impedance measurement result to the external device, or receive a variety of information which is conducive to the bioelectric impedance measurement from the external device.

In this case, the external device may be a medical apparatus using the measured bioelectric impedance information, a printer outputting a result, or a display device displaying the measured impedance information. In addition, the external device may be a smart phone, a mobile phone, a PDA, a laptop computer, a PC, and a mobile or non-mobile computing device, but is not limited thereto.

The communication unit 530 may communicate with the external device using Bluetooth communication, Bluetooth low energy (BLE) communication, near field communication (NFC), wireless local area network (WLAN) communication, Zigbee communication, infrared data association (IrDA) communication, wireless-fidelity (Wi-Fi) direct (WFD) communication, ultra-wideband (UWB) communication, Ant+ communication, Wi-Fi communication, radio frequency identification (RFID) communication, etc. However, those are merely an example and the communication is not limited thereto.

The analysis unit 540 may estimate a total body water (TBW), a body fat (FAT), a body fat ratio (% FAT), etc. based on the impedance of the object calculated by the impedance calculation unit 340 and object information (for example, a height, a weight, age, and gender, etc. of the object).

The user interface unit 550 may be a device for an interface of the bioelectric impedance measurement apparatus 500 and a user and/or other external devices, and include an input unit and an output unit. Here, the user may be a target for measuring the bioelectric impedance, that is, the object, but may have a concept broader than the object as a person who is capable of using the bioelectric impedance measurement apparatus 500 such as a medical expert.

Information needed for operating the bioelectric impedance measurement apparatus 500 may be input through the user interface unit 550, and the bioelectric impedance measurement result may be output. The user interface unit 550 may include a button, a connector, a keypad, a display, etc. Further, the user interface unit 550 may further include a component such as a sound output unit or a vibration motor, etc.

Figure 6:
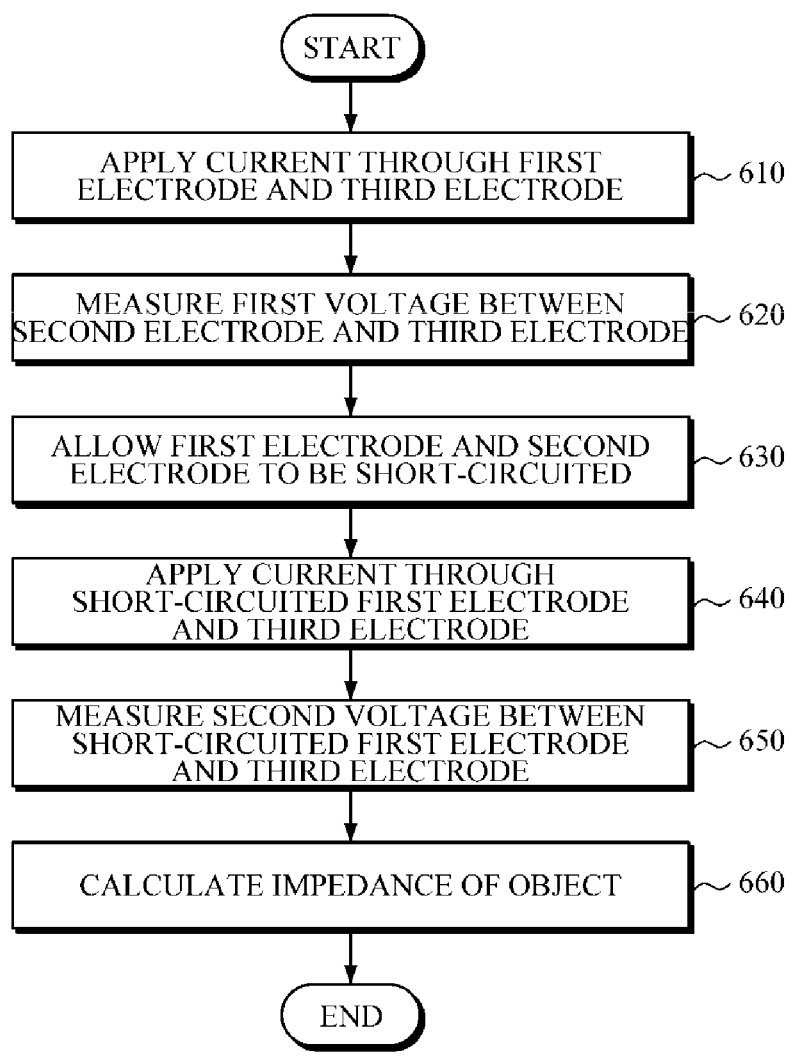
FIG. 6 is a flowchart for describing a bioelectric impedance measurement method according to an exemplary embodiment.

FIG. 6 is a flowchart for describing a bioelectric impedance measurement method according to an exemplary embodiment.

Referring to FIGS. 3 and 6, the bioelectric impedance measurement apparatus 300 may apply a predetermined current to an object using the first electrode 110 and the third electrode 130 (operation S610). In this case, the current may be an AC having a frequency of 1 Hz to 1 GHz.

The bioelectric impedance measurement apparatus 300 may measure a first voltage between the second electrode 120 and the third electrode 130 (operation S620).

The bioelectric impedance measurement apparatus 300 may allow the first electrode 110 and the second electrode 120 to be short-circuited (operation S630). The bioelectric impedance measurement apparatus 300 may operate the three electrodes 110, 120, and 130 as if they were two electrodes by allowing the first electrode 110 and the second electrode 120 to be short-circuited.

The bioelectric impedance measurement apparatus 300 may apply the predetermined current to the object using the short-circuited first electrode (or the short-circuited second electrode) and the third electrode 130 (operation S640).

The bioelectric impedance measurement apparatus 300 may measure a voltage (hereinafter, it may be referred to as a second voltage) between the short-circuited first electrode (or the short-circuited second electrode) and the third electrode 130 (operation S650).

The bioelectric impedance measurement apparatus 300 may calculate an impedance of the object based on the first voltage and the second voltage (operation S660). For example, the bioelectric impedance measurement apparatus 300 may calculate a first impedance using the first voltage and the current applied through the first electrode 110 and the third electrode 130, may calculate a second impedance using the second voltage and the current applied through the short-circuited first electrode (short-circuited second electrode) and the third electrode 130, and may calculate the impedance of the object based on the first impedance, the second impedance, and the bioelectric impedance calculation equation.

The bioelectric impedance calculation equation may define a relationship of the first impedance, the second impedance, and a bioelectric impedance, and be derived by considering a contact impedance generated by the contact of each electrode and the object. For example, the bioelectric impedance calculation equation may be expressed by Equation 1. Since the bioelectric impedance calculation equation was described above with reference to FIGS. 4A and 4B, a detailed description thereof will be omitted.

While not restricted thereto, an exemplary embodiment can be implemented as computer readable codes in a computer readable recording medium. Codes and code segments constituting the computer program can be easily inferred by a skilled computer programmer in the art. The computer readable recording medium includes all types of recording media in which computer readable data can be stored. Examples of the computer readable recording medium include a ROM, a RAM, a compact disk (CD)-ROM, a magnetic tape, a floppy disk, and an optical disk, etc. Further, the computer readable recording medium may be distributed to computer systems over a network in which computer readable codes may be stored and executed in a distributed manner. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A bioelectric impedance measurement apparatus comprising:
   a first electrode;
   a second electrode;
   a third electrode;
   a power supply connected between the first electrode and the third electrode during a first measurement and a second measurement;
   a short-circuit unit configured to leave the first electrode separated from the second electrode during the first measurement, and short-circuit the first electrode to the second electrode during the second measurement;
   a voltmeter connected between the second electrode and the third electrode during the first measurement and the second measurement, and configured to measure a first voltage between the second electrode and the third electrode while the power supply applies a current to an object through the first electrode and the third electrode, during the first measurement, and measure a second voltage between the short-circuited first electrode and the third electrode while the power supply applies a current to the object through the short-circuited first electrode and the third electrode, during the second measurement; and a processor configured to calculate a resulting impedance value of the object based on the first voltage and the second voltage.

2. The bioelectric impedance measurement apparatus of claim 1, wherein:

during the first measurement, the first electrode operates only as a current electrode, the second electrode operates only as a voltage electrode, and the third electrode operates both as a voltage electrode and a current electrode; and during the second measurement, the short-circuited first electrode operates both as a current electrode and a voltage electrode, and the third electrode operates both as a voltage electrode and a current electrode.

3. The bioelectric impedance measurement apparatus of claim 1, wherein the bioelectric impedance measurement apparatus is implemented as a wristwatch-type wearable device, and the first electrode and the second electrode are disposed on a back surface of a body of the wristwatch-type wearable device.

4. The bioelectric impedance measurement apparatus of claim 3, wherein the third electrode is disposed on a front surface of the body of the wristwatch-type wearable device.

5. The bioelectric impedance measurement apparatus of claim 3, wherein the third electrode is disposed on a strap of the wristwatch-type wearable device.

6. The bioelectric impedance measurement apparatus of claim 1, wherein the processor is further configured to calculate a first impedance based on the first voltage and the current applied to the object through the first electrode and the third electrode, calculate a second impedance based on the second voltage and the current applied to the object through the short-circuited first electrode and the third electrode, and calculate the resulting impedance value of the object based on the first impedance and the second impedance.

7. The bioelectric impedance measurement apparatus of claim 6, wherein the processor calculates the resulting impedance value based on a bioelectric impedance calculation equation defining a relationship of the resulting impedance value of the object, the first impedance, and the second impedance.

8. The bioelectric impedance measurement apparatus of claim 7, wherein the bioelectric impedance calculation equation is derived from a contact impedance generated by a contact between each electrode and the object.

9. The bioelectric impedance measurement apparatus of claim 1, wherein the first, second and third electrodes are further used to measure at least one of an electrocardiogram (ECG) and galvanic skin response (GSR).

10. The bioelectric impedance measurement apparatus of claim 1, wherein the processor is configured to calculate the resulting impedance value of the object only using the first electrode, the second electrode, and the third electrode.

11. A bioelectric impedance measurement method, comprising:

applying a current to an object through a first electrode and a third electrode during a first measurement, by using a power supply connected between the first electrode and the third electrode;

measuring a first voltage between a second electrode and the third electrode during the first measurement, by using a voltmeter connected to the second electrode and the third electrode;

short-circuiting the first electrode to the second electrode during a second measurement;

applying a current to the object through the short-circuit first electrode and the third electrode during the second measurement, by using the power supply connected between the first electrode and the third electrode;

measuring a second voltage between the short-circuited first electrode and the third electrode during the second measurement, by using the voltmeter connected to the second electrode and the third electrode; and calculating a resulting impedance value of the object based on the first voltage and the second voltage.

12. The bioelectric impedance measurement method of claim 11, wherein the calculating the resulting impedance value of the object comprises:

calculating a first impedance based on the first voltage and the current applied to the object through the first electrode and the third electrode;

calculating a second impedance based on the second voltage and the current applied to the object through the short-circuited first electrode and the third electrode; and calculating the resulting impedance value of the object based on the first impedance and the second impedance.

13. The bioelectric impedance measurement method of claim 12, wherein the calculating the resulting impedance value of the object uses a bioelectric impedance calculation equation defining a relationship of the resulting impedance value of the object, the first impedance, and the second impedance.

14. The bioelectric impedance measurement method of claim 13, wherein the impedance calculation equation is derived from a contact impedance generated by a contact between each electrode and the object.

* * * * *